United States Patent [19]

Elgebaly

[11] Patent Number: 5,606,027
[45] Date of Patent: Feb. 25, 1997

[54] ANTIBODIES TO A NEUTROPHIL CHEMOTACTIC PROTEIN

[76] Inventor: Salwa A. Elgebaly, 22 Silo Way, Bloomfield, Conn. 06002

[21] Appl. No.: 404,027

[22] Filed: Mar. 14, 1995

Related U.S. Application Data

[63] Continuation-in-part of Ser. No. 975,640, Nov. 13, 1992, Pat. No. 5,403,914, which is a continuation-in-part of Ser. No. 852,890, Mar. 3, 1992, abandoned, which is a continuation of Ser. No. 649,154, Feb. 1, 1991, abandoned, which is a continuation of Ser. No. 107,280, Oct. 9, 1987, abandoned.

[51] Int. Cl.$^6$ ............................................. C07K 16/24
[52] U.S. Cl. ................................. 530/389.2; 530/351
[58] Field of Search ..................... 530/388.23, 388.85, 530/389.2

[56] References Cited

U.S. PATENT DOCUMENTS

| | | | |
|---|---|---|---|
| 4,797,277 | 1/1989 | Arfors | 424/85.8 |
| 5,079,228 | 1/1992 | Cohen et al. | 514/12 |
| 5,403,914 | 4/1995 | Elgebaly | 530/324 |

OTHER PUBLICATIONS

Elgebaly et al., Circulation 88(4 Part 2) 1993 p. I240 Abstract #1285.
Sticherling et al., J. Immunol. 143:1628–1634 1989.
Benedict R. Lucchesi, et al, "Leukocytes and Ischemia-Induced Myocardial Injury", *Ann. Rev. Pharmacol. Toxicol.* 1986, 26:201–24.
Salwa A. Elgebaly, PhD, et al, "Releases of Neutrophil Chemotactic Factors from Ischemic Myocardial Tissues", *Am. College of Surgeons 1987 Surg. Forum*, vol. 38, pp. 276–279.
Salwa A. Elgebaly, et al, "In Vitro Detection of Cornea-Derived Leukocytic Chemotactic Factors as Indicators of Corneal Inflammation", *In Vitro Toxicology Approaches to Validation*, Mary Ann Liebert, Inc., New York, NY, 1987, pp. 257–268.
Salwa A. Elgebaly, PhD, et al, "Characterization of Neutrophil and Monocyte Specific Chemotactic Factors Derived . . .", *AJP*, vol. 126, No. 1, Jan. 1987, pp. 40–50.
Sally H. Zigmond et al, "Leukocyte Locomotion and Chemotaxis", *The Journal of Experimental Medicine*, vol. 137, 1973, pp. 387–410.
Eberhard Schröder and Klaus Lübke, *The Peptides*, vol. I, Academic Press, New York and London, p. xxiv.

*Primary Examiner*—Marian C. Knode
*Assistant Examiner*—Nancy A. Johnson
*Attorney, Agent, or Firm*—Chilton, Alix & Van Kirk

[57] ABSTRACT

Antibodies to a neutrophil chemotactic protein (NOURIN-I) specific to that protein are provided. The antibodies can be used in diagnostic assays and as pharmaceutical agents. The chemotactic protein represents the initial signal that recruits neutrophils to injured tissue and exhibits a molecular weight of approximately 3 KDa and an isoelectric point of pH 7–8.

4 Claims, 9 Drawing Sheets

FIG. 4
HPLC/HEART

| Graph Symbol | Assay Symbol | Assay Antibody |
|---|---|---|
| ● | IEF-pooled fractions containing Nourin-1 | Culture supernatant from 1x cloned anti-Nourin-1 hybridoma (1A3) |
| △ | IEF-pooled non-chemotactically active fractions | 1A3 |
| ■ | IEF-pooled fractions containing Nourin-1 | Non-specific mouse IgG |

ANTIBODIES TO A NEUTROPHIL CHEMOTACTIC PROTEIN

RELATED APPLICATIONS

This application is a continuation in part of my application Ser. No. 07/975,640 filed Nov. 13, 1992, now U.S. Pat. No. 5,403,914, which is a continuation in part of application Ser. No. 07/852,890 filed Mar. 3, 1992, now abandoned, which is a continuation of application Ser. No. 07/649,154 filed Feb. 1, 1991, now abandoned, which is a continuation of application Ser. No. 07/107,280 filed Oct. 9, 1987, now abandoned.

BACKGROUND OF THE INVENTION

The present invention relates generally to antibodies to biological mediators of immune function. More specifically, it is concerned with antibodies to a purified and isolated leukocyte chemotactic protein released by injured tissue (hereinafter NOURIN-I).

Biological mediators such as leukocyte chemotactic factors stimulate the migration of neutrophils from circulation into sites of infection or tissue damage. These mediators are also believed to increase cell adhesion to injured sites and to activate neutrophils to release toxic agents such as oxygen metabolites and proteases. Due to their important role, the nature and source of these mediators have been extensively studied. It has been believed they are primarily derived from low molecular weight serum protein components, that is, from complement-split products C3a and C5a and fibrin-split peptide products as well as from activated immune cells such as leukotriene $B_4$, $LTB_4$, and interleukin-8, IL-8. Type I collagen peptide products and the synthetic tripeptide f-Met-Leu-Phe are also chemotactically active for both neutrophils and mononuclear cells.

However, the initial signals that recruit and activate the neutrophils have not been defined and it is not known whether injured tissue directly participates in the influx of circulating leukocytes by releasing mediators which recruit neutrophils to the sites of the injury.

It has now been found, as described in my copending application Ser. No. 07/975,640 filed Nov. 13, 1992, now U.S. Pat. No. 5,403,914 that a high level of neutrophil chemotactic factor is released by tissues such as coronary arteries and myocardial tissue under ischemic conditions. In addition to the cardiovascular-derived neutrophil chemotactic factors, substantially the same factor has been detected in spinal cord, brain, cornea, retina, conjunctiva, stomach, vein grafts and urinary bladder. This neutrophil chemoattractant is believed to represent the "initial signal" that recruits neutrophils to the tissue shortly after injury induced chemical agents, physical trauma, ischemia, and endotoxin treatments. They differ in their biochemical characteristics and molecular weight from previously known factors, such as the complement split products C3a and C5a having molecular weights of about 11,000 daltons (11 KDa) and leukocyte products such as IL-8 and $LTB_4$ that have molecular weights of 10 KDa and 366 Da, respectively. As released from the tissue, the factor exists as a protein complex having a molecular weight of about 100 KDa to 300 KDa. The complex is a positively charged unit consisting of a weakly associated high molecular weight co-factor or carrier and a low molecular weight greater than 500 Da, but less than 5 KDa, active factor that carries an apparent neutral or negative charge. From sodium dodecyl sulfate-polyacrylamide gel electrophoresis (SES-PAGE) analysis, the purified protein (NOURIN-I) corresponding to the chemotactively active band has a molecular weight of 3 KDa. The protein has an isoelectric point of pH 7–8 for the cardiac derived factor, while the cornea-derived factor has a slightly higher isoelectric point of pH 8.5. It is clearly different from the previously known factors C3a, C5a, IL-8 and $LTB_4$ which appear to play important roles as "late signals" that recruit additional neutrophils to infarcted myocardium and to regions where activated neutrophils exist, such as inflamed myocardium.

SUMMARY OF THE INVENTION

It is an object of the present invention to provide an antibody to the neutrophil chemotactive factor protein designated NOURIN-I which specifically recognizes that protein. Included in this object is the provision for new polyclonal and monoclonal antibodies to NOURIN-I.

Another object of the present invention is to provide antibodies to a new protein-like factor or factors of the type described that will allow better clinical management of patients with cardiovascular inflammation including heart attack patients, those with unstable angina, and patients undergoing heart surgery, organ transplant, or similar procedures to control and regulate the recruitment and activation of cells associated with acute inflammatory reactions.

A further object of the present invention is to provide antibodies to a chemotactic mediator of the type described that is found in a variety of tissues and in various species, the mediators being tissue specific and capable of signaling the initial non-physiological condition of the tissue, particularly the stimulation of neutrophil migration during reperfusion following ischemia as seen in open heart surgery, organ transplant, and the like.

A still further feature of the present invention is the provision for a new and improved procedure for concentrating, isolating, and at least partially purifying the neutrophil chemotactic factor of both the complex and its dissociated components by injured tissue such as ischemic myocardial and coronary arterial tissue. Included in this is the provision for the concentration, purification and isolation of a chemotactic factor that differs from known neutrophil chemotactic factors, is not released from serum or white blood cells and is of a molecular weight that is significantly different from the molecular weight of known factors such as those mentioned heretofore. This neutrophil chemoattractant advantageously differs in its biochemical characteristics and is believed to play an important role in leukocyte infiltration associated with tissue inflammation and repair.

Another object of the present invention is to provide antibodies to an inflammatory mediator for myocardial and/or coronary arterial tissue that is released under ischemic conditions, that is, under conditions of nonspecific injury. The mediator is a neutrophil chemoattractant that stimulates the migration of circulating leukocytes into injury sites. This new mediator differs in its biochemical characteristics from serum-derived and immune cell-derived factors. Included in this object is the provision for monoclonal and polyclonal antibodies specific to the chemotactic mediator.

Other objects and advantages will be in part obvious and in part pointed out more in detail hereinafter.

These and related objects are achieved in accordance with the present invention by providing antibodies to a purified and isolated biological mediator comprising an active low molecular weight neutrophil chemotactic protein designated NOURIN-I. The antibodies provide a unique therapy approach to the regulation of NOURIN-I and therefore to the recruitment of neutrophils associated with tissue inflammation and repair and may be used to produce markers and blockers.

The invention also comprises salts, functional derivatives and active fractions of the antibodies and of the fragments thereof. As used herein, the term "salts" refers both to salts of carboxyl groups and to acid addition salts of amino groups of the protein molecule. "Functional derivatives" as used herein covers derivatives which may be prepared from the functional groups which occur as side chains on the residues or the N- or C-terminal groups, by means known in the art. As "active fractions" of the antibodies and their fragments, the present invention covers any fragment or precursors of the polypeptide chain of said protein molecules alone or together with associated molecules or residues linked thereto, e.g., sugar or phosphate residues, or aggregates of the protein molecule or the sugar residues by themselves.

The invention further relates to the use of said antibodies and of fragments thereof, and salts, functional derivatives or active fractions of said antibodies and fragments, as pharmaceutical agents and as markers or blocking agents.

Another aspect of the invention features the diagnostic use or tests for measuring either NOURIN-I or the antisera against it, based on determining the interaction of the antibodies with NOURIN-I. These diagnostic uses are of two kinds: (a) detecting endogenously produced antibodies to NOURIN-I in body fluids, to determine the extent to which such antibodies contribute to pathological manifestations of injury or disease, and (b) quantifying the levels of NOURIN-I in body fluids to detect or measure over- or under-production of this protein in any disorder or injury characterized by abnormal production of the protein.

A better understanding of the invention will be obtained from the following detailed description and the accompanying drawing as well as from the illustrative applications of the invention including the several components thereof and the relationship of one or more of such components with respect to each of the others as well as the features, characteristics, compositions, properties and relation of elements described and exemplified herein.

DESCRIPTION OF A PREFERRED EMBODIMENT

The leukocyte chemotactic factors described in my copending U.S. patent application Ser. No. 07/975,640 now U.S. Pat. No. 5,403,914 may be generated and isolated by initially inducing a nonphysiological condition such as stress or injury to the tissue. While ischemia in myocardial and coronary tissue were used for ease of understanding and clarity of description and illustration, the invention has application to other non-physiological conditions, including physical trauma, microbial infection and/or chemical exposure, and to a variety of species, such as human, canine, rabbit, bovine, porcine and chicken, and to a variety of other tissues, such as spinal cord, brain, cornea, retina, conjunctiva, stomach, vein graft and urinary bladder.

The ischemic condition was induced experimentally both in vivo by clamping the aorta or coronary artery and in vitro by subjecting isolated hearts to perfusion or incubating intact or cut hearts or heart segments with freshly prepared crystalloid cardioplegia or phosphate buffered saline (PBS). For human studies, coronary sinus effluents were collected from patients undergoing aortocoronary bypass. Samples were collected prior to and during aortic cross-clamping at fixed intervals and one hour after cross-clamping.

Figure 1:
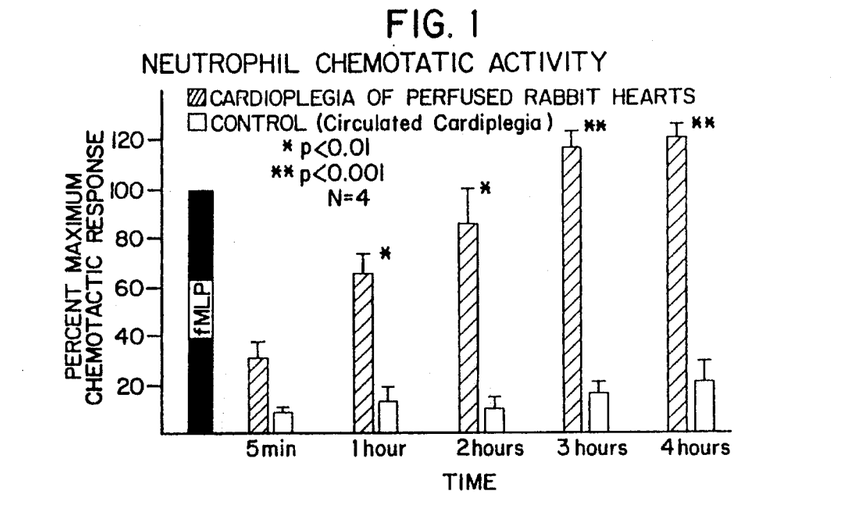
FIGS. 1, 2 and 3 are graphs showing neutrophil chemotactic activity in various tissues as a function of time and maximum chemotactic response.
Figure 2:
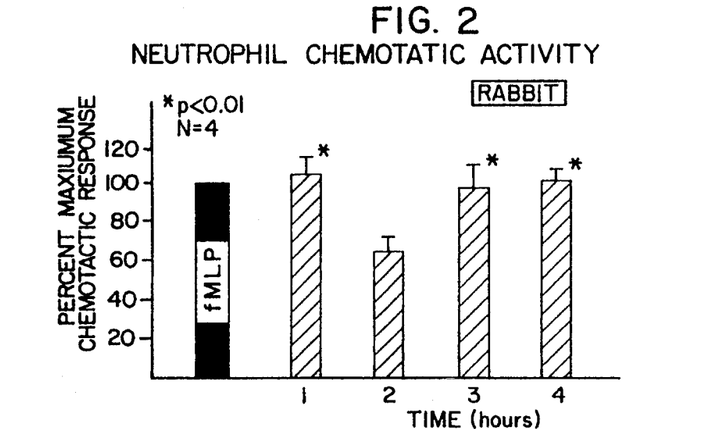
Figure 3:
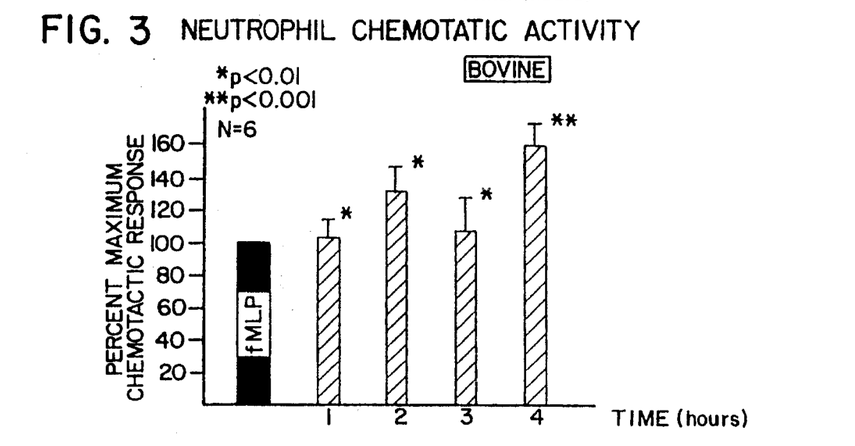
Figure 4:
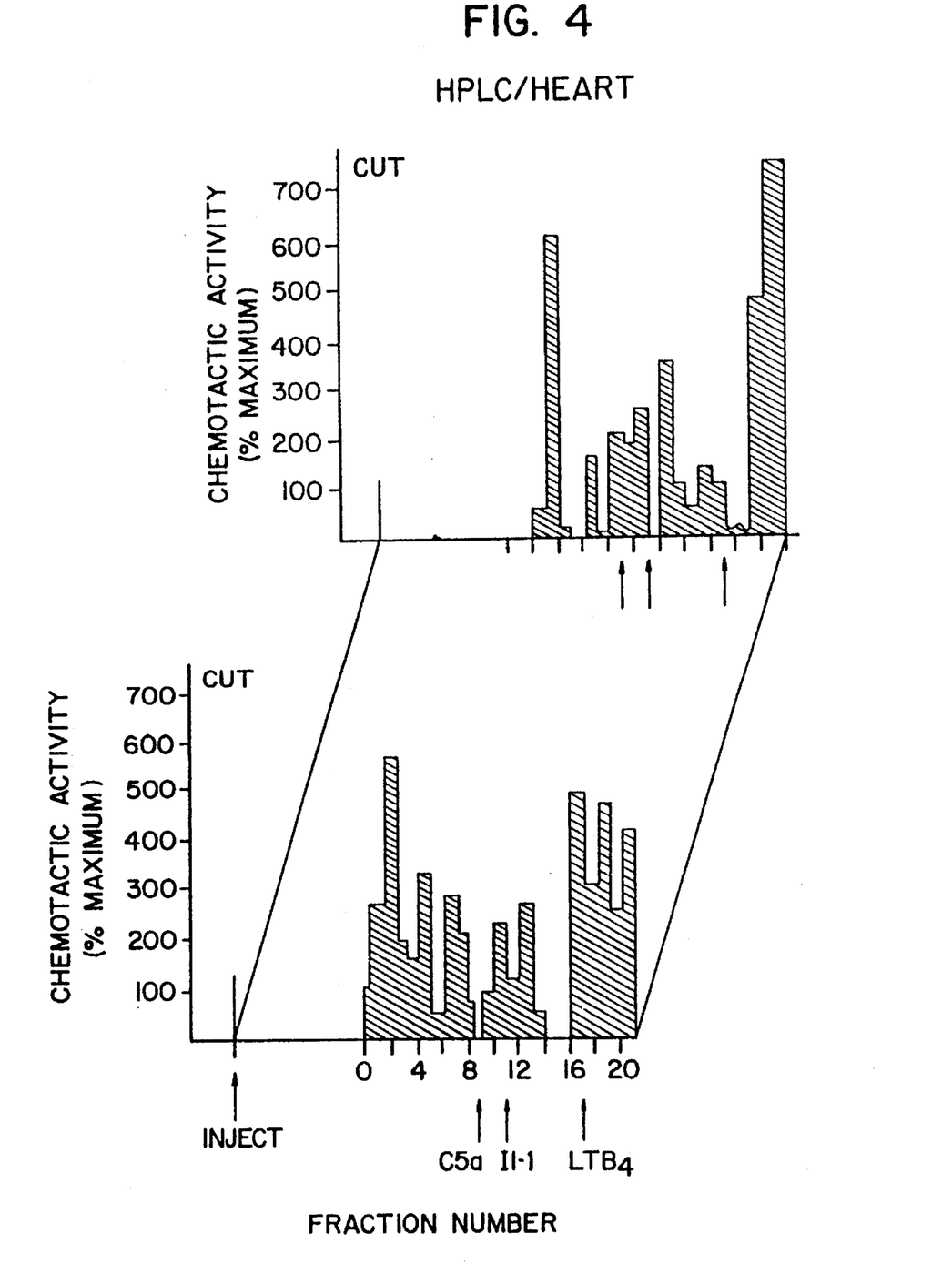
FIG. 4 graphically depicts the chemotactic activity of separated chromatographic fractions.
Figure 5:
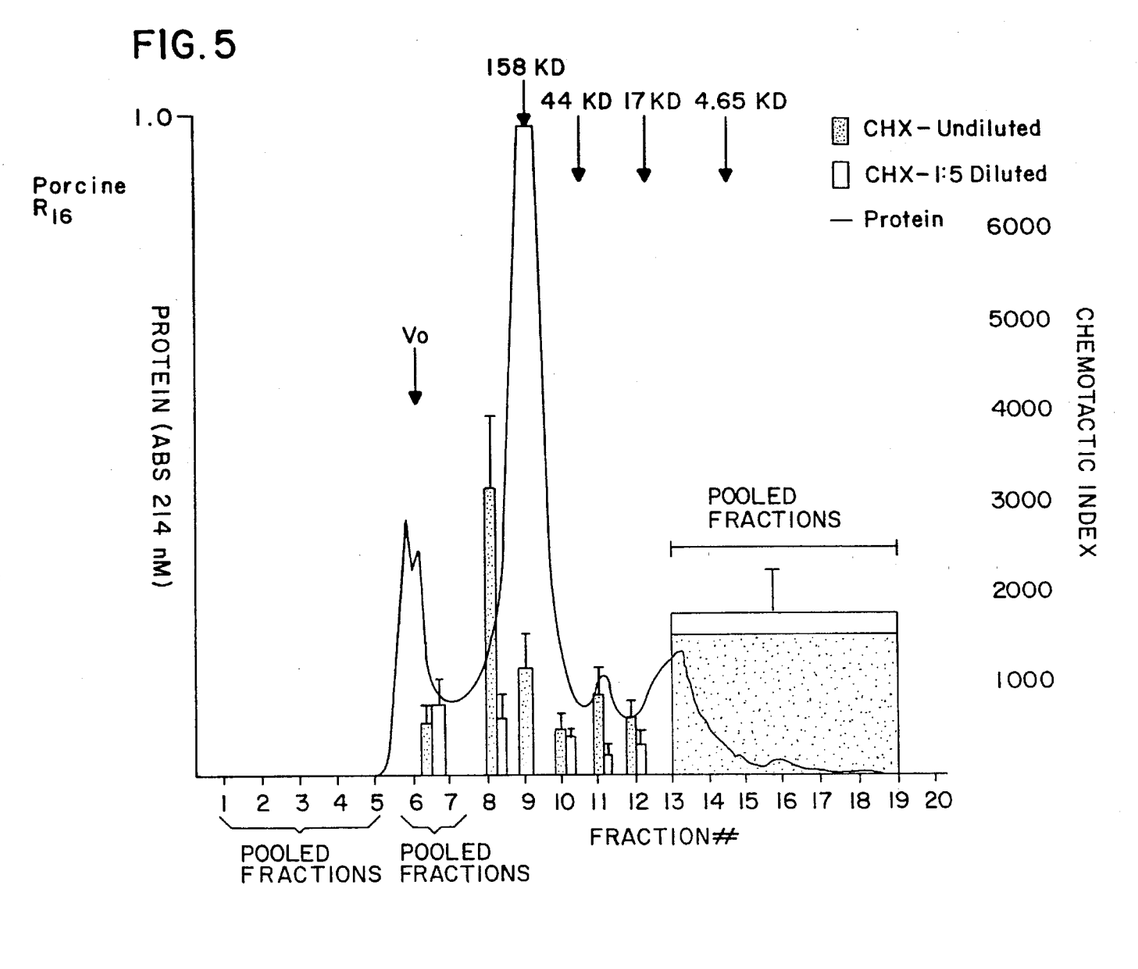
FIG. 5 is a graph showing neutrophil chemotactic activity and protein elution profile in various fractions isolated from test animals.

For determining whether neutrophil chemoattractants were released, myocardial segments were obtained from isolated rabbit, bovine and porcine hearts. Typical results are shown graphically in FIGS. 1, 2 and 3. All data are expressed as mean values plus or minus the standard error of the mean.

Figure 7:
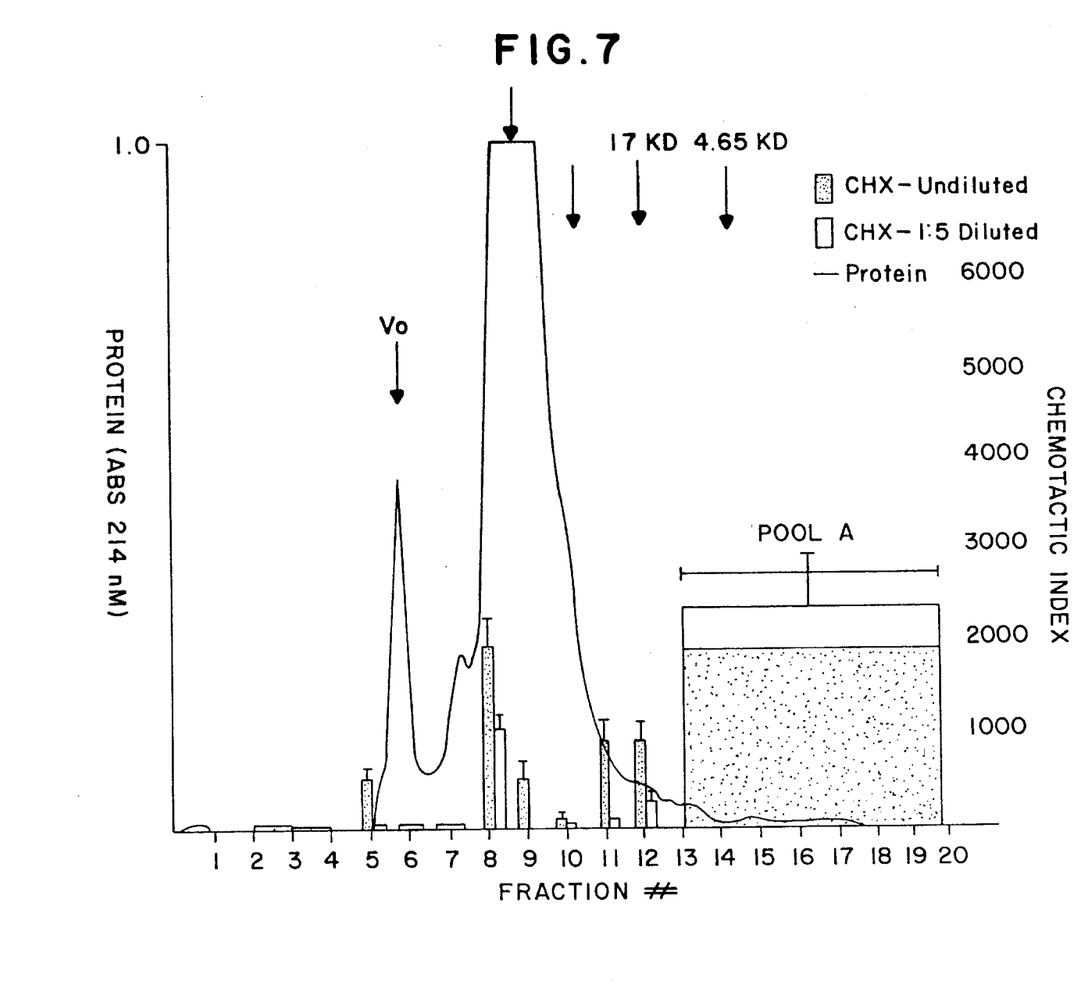
Figure 8:
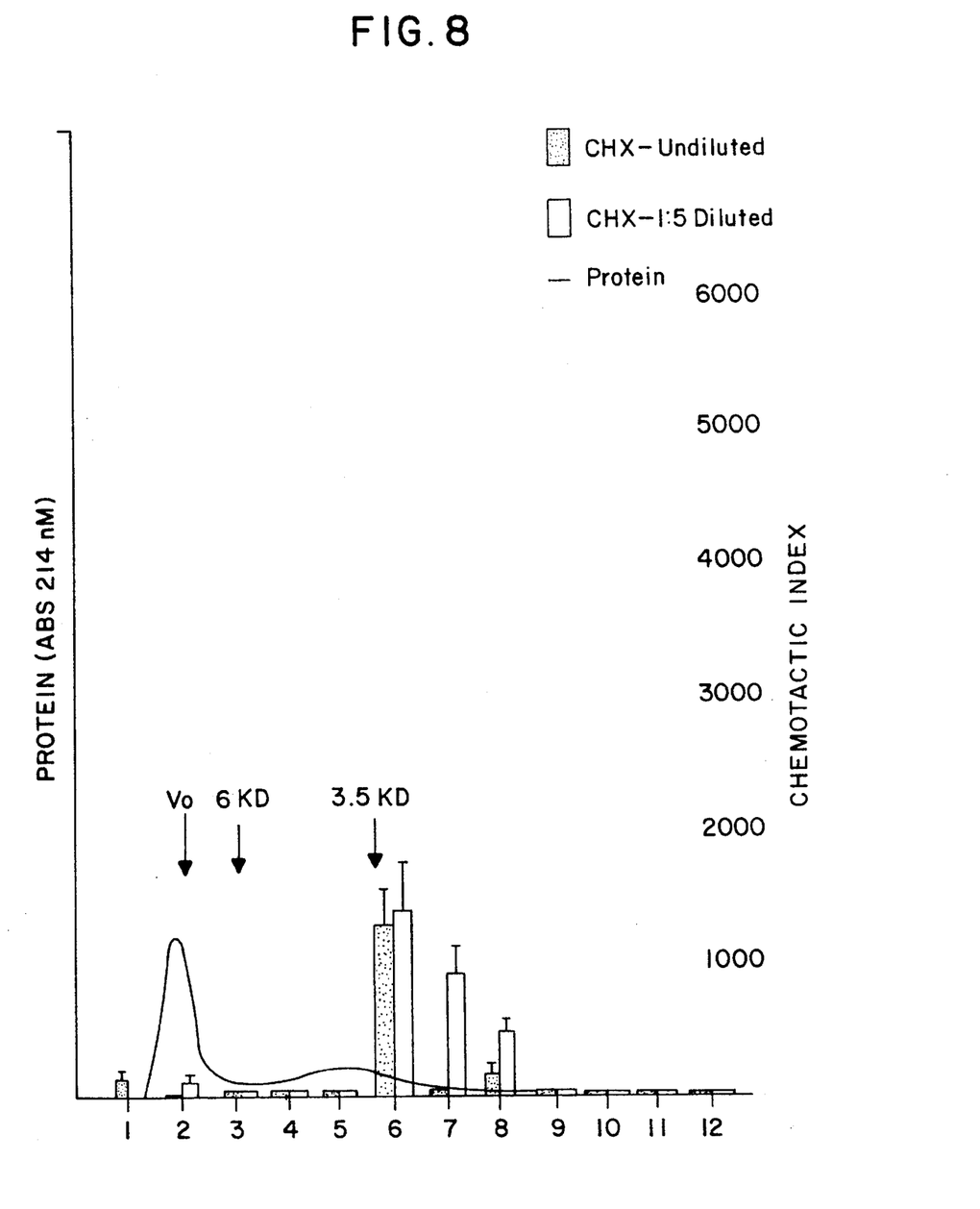
FIG. 8 is a graph similar to FIGS. 5–7 of fractions 13–20 of FIG. 7.

Cardioplegic solutions were collected during cardiac arrest from patients who underwent aortocoronary artery bypass. The samples were individually concentrated and then fractionated using size exclusion high performance liquid chromatography, HPLC, which discriminates in a molecular weight range of 1 to 300 KDa. The chromatographic fractions were then tested for neutrophil chemotactic activity. The activity was recovered in peaks eluted at 100–300 KDa and less than 5 KDa. These two peaks or regions of chemotactic activity can be seen in FIGS. 4–7 but are best noted in FIG. 6. When fractions between 500 Da and 5 KDa were further fractionated, activity was detected in a peak eluted at 3 KDa. Chemotactic activity was increased with dilution, as shown in FIG. 8, a response commonly noted with chemotactic factors. Using enzyme linked immunosorbent assay (ELISA) and standard radio immunoassay (RIA), it has been found that $LTB_4$, IL-8, and C5a factors were not detected in coronary sinus effluent samples used to purify the 3 KDa cardiac NOURIN-I.

The antibodies of the present invention may be either polyclonal or monoclonal. They may be raised in rabbits, mice or other animals or tissue cultured cells derived thereof or can be products of cells of human origin. They may also be produced by recombinant DNA technology either in a form identical to that of the native antibody or as chimeric molecules, constructed by recombination of antibody molecules of man and animal origins or in other forms chosen to make the antibodies most suitable for use in therapy.

For the preparation of the antibodies, isolated and purified 3 KDa protein NOURIN-I may be used to immunize the animals. Conventional techniques (Ida N., et al (1992) J. Immunol Meth. 156:27–38) may be used to develop the polyclonal antibodies against human cardiac NOURIN-I.

Figure 9:
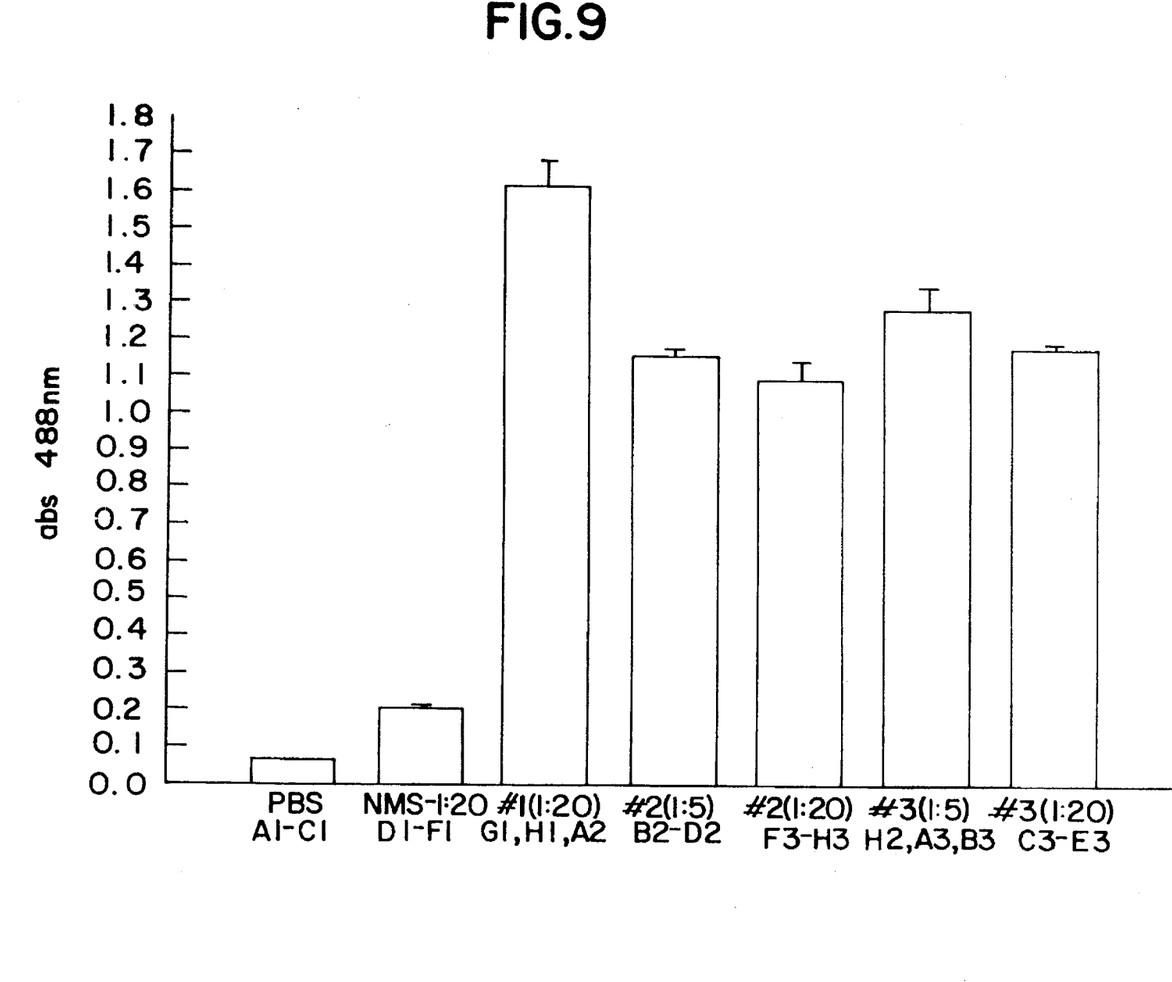
FIG. 9 is a graph showing the results of an ELISA screening for antibodies.

Results of ELISA screening for the polyclonal antibody to NOURIN-I are graphically illustrated in FIG. 9 at dilutions of 1:5 and 1:20. The quantitative absorbance values were read at 488 nm. A further possibility is to fuse one of the possible nucleotide sequences coding for a fragment of NOURIN-I to the gene coding for Protein A, to express the fused Protein A-NOURIN-I gene in *E. coli*, to purify the fused protein by affinity chromatography on IgG Sepharose column and then to use it to immunize animals.

Figure 11:
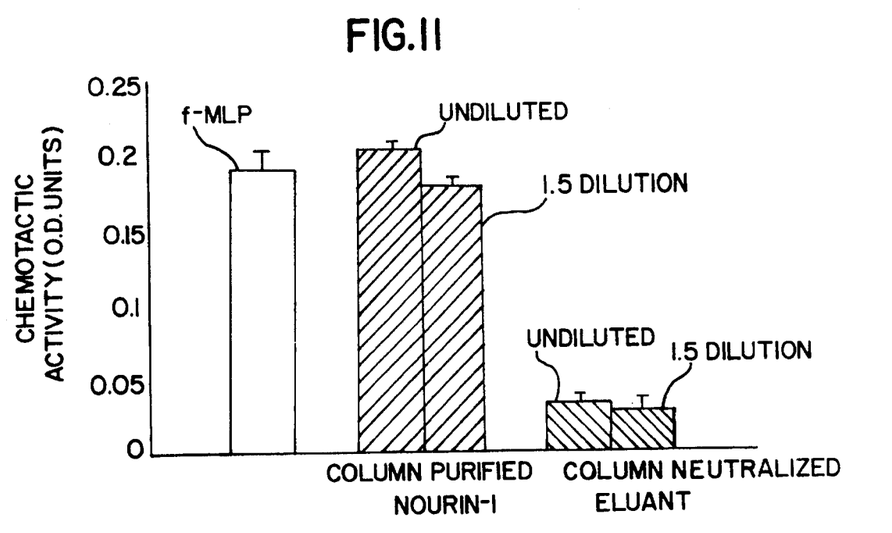
FIG. 11 is a graph showing the blocking of neutrophil migration using the monoclonal antibody.

The monoclonal antibodies of the present invention are prepared using conventional hybridoma technique (Mishell and Shiigi, *Selected Methods in Cellular Immunology*, published by W. H. Freeman Co., San Francisco, 1980). After immunization, spleen cells of the immunized animals are isolated and fused or hybridized with a suitable myeloma cell line. After fusion, the resulting hybridoma cells are collected and used to assay by ELISA for specificity. The results are shown in FIG. 11 and indicate that the monoclonal antibody shows specificity for NOURIN-I only.

The monoclonal antibodies may also be immobilized and used for the purification of the NOURIN-I in affinity purification procedure using an immunoadsorbent column.

Pharmaceutical compositions of the antibodies can be prepared from a pharmaceutically acceptable carrier and an antibody to NOURIN-I or a fraction thereof or salts, functional derivatives, precursors or active fractions thereof or mixtures of any of the foregoing, as active ingredient. The manner of administration can be via any of the accepted modes of administration for similar agents and will depend on the condition to be treated. The pharmaceutical compositions are prepared for administration by mixing the protein or its derivatives with physiologically acceptable carriers, stabilizers and excipients, and prepared in dosage form, e.g., by lyophilization in dosage vials. The amount of active compound to be administered will depend on the route of administration, the disease to be treated and the condition of the patient.

The following examples are given in order that the effectiveness of the present invention may be more fully understood. These examples are set forth for the purpose of illustration only, and are not intended in any way to limit the practice of the invention. Unless otherwise specified, all parts are given by weight.

EXAMPLE I

Preparation of Purified NOURIN-I

Figure 6:
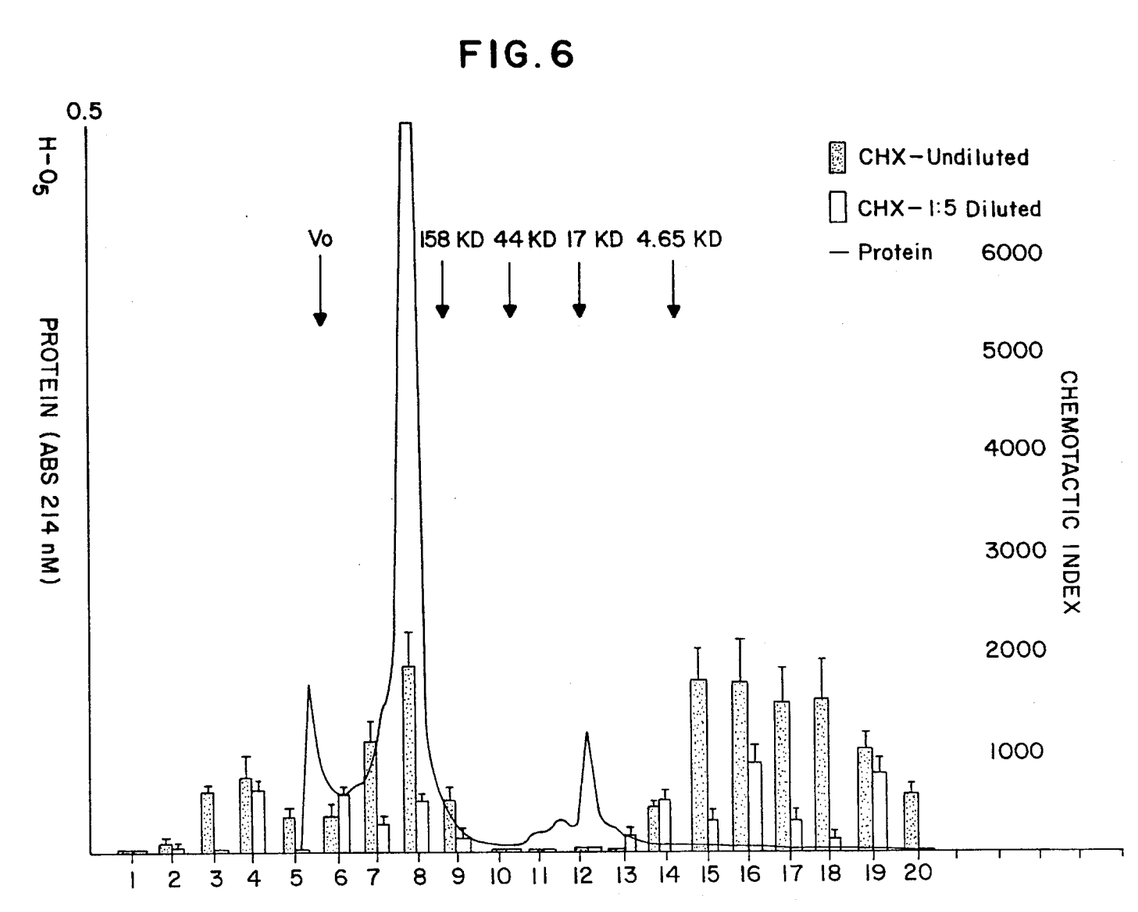
FIGS. 6 and 7 are graphs similar to FIG. 5 for fractions isolated from coronary sinus effluents collected from human patients during open heart surgery for myocardial revascularization.

Cardioplegic solutions were collected during cardiac arrest from patients undergoing aortocoronary artery bypass for treatment of symptomatic coronary artery occlusive disease. Twelve patients' effluent samples were individually concentrated using Amicon ultrafiltration membrane (MWCO 500 Da). The resulting samples were then fractionated using size exclusion high performance liquid chromatography (HPLC) on a column which discriminates in the molecular weight range of 1–300 KDa. As shown in FIG. 6 and FIG. 7 representative of 12 different patients, chemotactic activity was detected in peaks eluted at a correspondingly high molecular weight range of 100–300 KDa and a low molecular weight range of less than 5 KDa for both the starting samples (FIG. 6) and the retentates (FIG. 7).

Fractions 13–20 of FIG. 7 of molecular weight less than 5 KDa were fractionated on a size exclusion HPLC column having a molecular weight range of 1–6 KDa, using Biorad-Econo Pac-6. Fractions were eluted off the column and tested for neutrophil chemotactic activity. As can be seen in FIG. 8, chemotactic activity was detected in a peak eluted at approximately 3 KDa. Using concentrated fractions of the less than 5 KDa material, isoelectric focusing was performed and indicated that chemotactic activity co-migrated with ampholytes having an isoelectric point of approximately pH 7–8. No chemotactic activity was detected in adjacent fractions. Isoelectric focusing data gives support to the ion exchange characterization of the low molecular weight fraction as being a neutral to negative protein. SDS-PAGE followed by silver staining showed a protein band at 3 KDa. This band area, which was excised from a gel ran in parallel with the stained gel, was found to contain a chemotactically active material for rabbit and human neutrophils whereas a blank area of the gel was inactive. The isolated and purified 3 KDa protein is referred to NOURIN-I.

EXAMPLE II

Preparation of Polyclonal Antibodies against NOURIN-I

Mouse polyclonal antibodies were generated against a purified NOURIN-I (isoelectric focusing active fraction of pH 7–8) using the following procedure.

Three mice were immunized with 20 ug of purified NOURIN-I in complete Freund adjuvant. After a 3 week incubation period, these mice were injected again using 20 ug NOURIN-I in complete Freund adjuvant. Seven days later, blood was drawn separately from the immunized mice as well as from one non-immunized mouse (control). Seras were screened for antibody titer using a standard ELISA. Microtiter plate wells were coated with purified NOURIN-I (0.5 ug/well). Phosphate buffered saline (PBS) was placed in the first well group, non-immunized mouse sera in the second, and immunized mouse sera were added to the remaining wells at dilutions of 1:5 and 1:20 and the plate was incubated at 37° C. for one hour. Following plate washes, antimouse conjugated peroxidase antibody was added and incubated for an additional hour at 37° C. To allow the horse radish peroxidase development, 1,2phenylenediamine was added. The microtiter plate was read at 488 nm.

The results are graphically shown in FIG. 9 and indicate the presence of antibody in only mice immunized against NOURIN-I at both 1:5 and 20 dilutions. PBS and control sera from the non-immunized mouse did not show any antibody titer.

EXAMPLE III

Development of Monoclonal Antibodies to NOURIN-I

Spleen cells from immunized mice which showed a positive antibody response to NOURIN-I were hybridized with cells from a mouse myeloma, non-secreting P3X63-AG8.653. Monoclonal antibody from culture supernatant layers from one time cloned hybridomas against NOURIN-I were collected and used to assay by ELISA for its specificity. Microtiter plate wells were coated with either purified NOURIN-I (0.5 ug/well) obtained from pooled isoelectric focusing fractions of pH 7–8, or non-chemotactically active isoelectric focusing fractions adjacent to fractions containing NOURIN-I. The assay antibody included either culture supernatant media from the cloned anti-NOURIN-I hybridoma or non-specific mouse immunoglobulin G (IgG).

Figure 10:
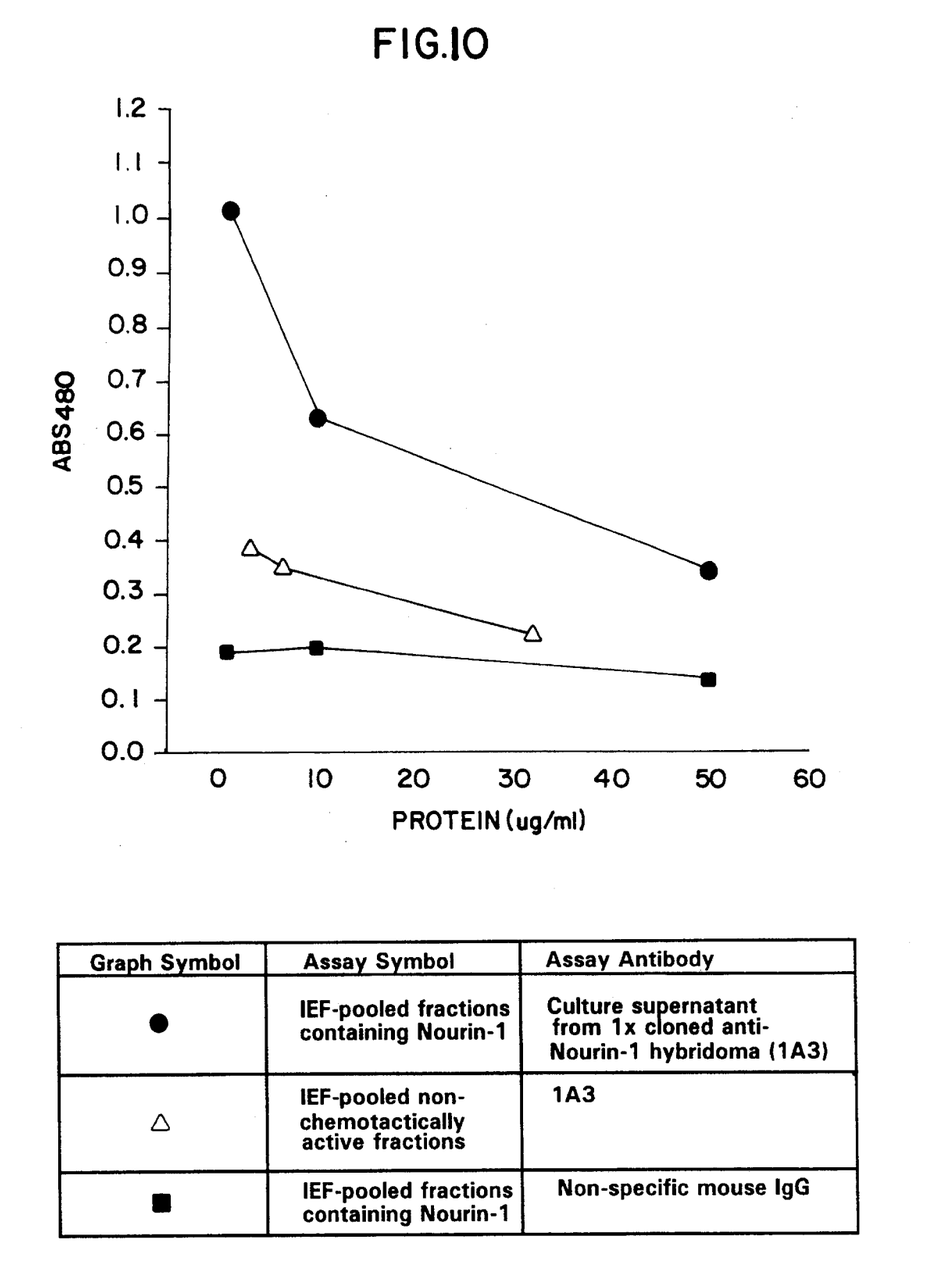
FIG. 10 is a graph showing the specificity of the monoclonal antibody for NOURIN-I only.

Plates were then incubated at 37° C. To allow the horseradish peroxidase development, 1,2-phenylenediamine was added. Microtiter plates were read at 480 nm. As shown in FIG. 10, the monoclonal antibody showed specificity for NOURIN-I only and not for the sample containing non-chemotactically active protein. The non-specific mouse IgG did not react with NOURIN-I.

EXAMPLE IV

Monoclonal Antibody against NOURIN-I Neutralizes Cell Migration

The purified monoclonal antibody against NOURIN-I was coupled to a hydrazide gel affinity column which is an agarose support that reacts with the aldehydes of oxidized carbohydrates to form stable covalent hydrazone bonds. This eliminates the loss of antibody activity experienced in primary amino coupling at or near the antigen binding site.

Using up to 3 ml of the purified antibody, it was applied to the hydrazide coupled column to couple the antibody to the column. Samples of cardiac derived NOURIN-I obtained from isoelectric focusing then were applied to the column. The eluant was monitored spectrophotometrically at 280 nm and tested for chemotactic activity. As shown in FIG. 11, the antibody coupled column bound the NOURIN-I and neutralized the eluant as evidenced by the significant reduction in chemotactic activity in both undiluted form and when diluted 1:5.

EXAMPLE V

Monoclonal Antibody against NOURIN-I Neutralizes IL-8 Stimulating Effect of NOURIN-I It has been found that NOURIN-I stimulates the secretion of interleukin-8 (IL-8). Peripheral blood samples from healthy volunteers were incubated with 25 ug/ml of NOURIN-I. After 4 hours and 24 hours, the solutions were assayed for levels of IL-8 by ELISA.

Figure 12:
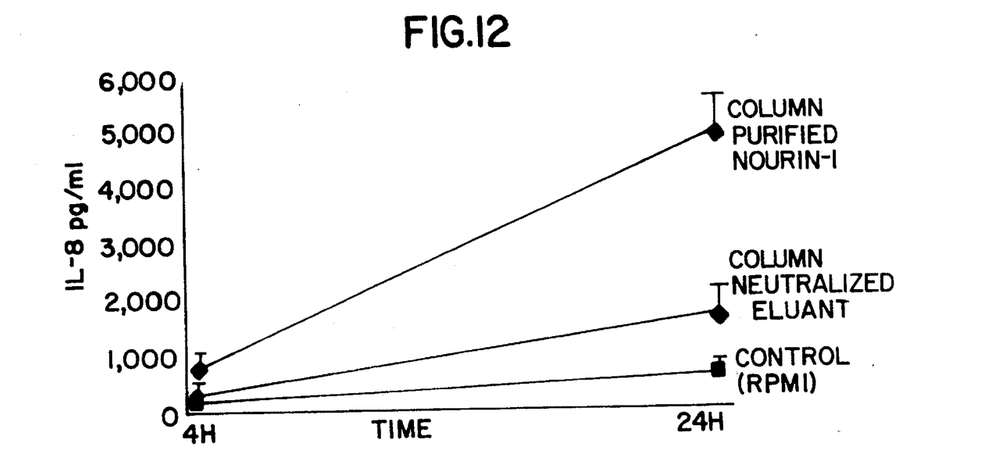
FIG. 12 is a graph showing the blocking of interleukin-8 secretion using the antibody.

The same procedure was followed using the column neutralized eluant of Example IV. As shown in FIG. 12, the antibody neutralized eluant blocked IL-8 secretion from 4800 pg/ml IL-8 to approximately 1200 pg/ml. This neutralization of the stimulating effect of NOURIN-I by the antibody also is an indication of the specificity of the response by NOURIN-I to the antibody.

EXAMPLE VI

Specificity of Antibody to NOURIN-I

The procedure of Example IV was repeated except that purified human IL-8 was used in place of the purified NOURIN-I. Eluant from the column was monitored at 280 nm and assayed for IL-8 by ELISA. The column bound antibody did not recognize or bind any of the purified IL-8 eluted through the column.

As will be apparent to persons skilled in the art, various modifications, adaptations and variations of the foregoing specific disclosure can be made without departing from the teachings of the present invention.

I claim:

1. An antibody to NOURIN-I, a biological mediator of immune function for stimulating neutrophil activity, said mediator being a protein having the following physicochemical characteristics: a molecular weight within the range of about 500 to 5,000 daltons, as determined by calibrated gel filtration, protease sensitivity, heat instability, non-leukotriene, non-interleukin, non-serum derived, non-immune cell derived and will stimulate neutrophil degranulation, said antibody having specificity for said protein.

2. An antibody according to claim 1 which is a polyclonal antibody.

3. An antibody according to claim 1 wherein said neutrophil chemoattractant protein has a molecular weight of approximately 3000 daltons as determined by SDS polyacrylamide gel electrophoresis.

4. An antibody according to claim 1 wherein said protein has an isoelectric point of pH 7–8.

* * * * *